United States Patent
West et al.

(10) Patent No.: US 7,175,741 B2
(45) Date of Patent: Feb. 13, 2007

(54) REDUCING ODOR IN ABSORBENT PRODUCTS

(75) Inventors: Hugh West, Seattle, WA (US); Colin Elston, Gig Harbor, WA (US); David DeJong, Buckley, WA (US)

(73) Assignee: Weyerhaeuser, Co., Federal Way, WA (US)

( * ) Notice: Subject to any disclaimer, the term of this patent is extended or adjusted under 35 U.S.C. 154(b) by 0 days.

(21) Appl. No.: 10/621,779

(22) Filed: Jul. 16, 2003

(65) Prior Publication Data

US 2005/0011623 A1 Jan. 20, 2005

(51) Int. Cl.
*D21H 11/00* (2006.01)

(52) U.S. Cl. .................. 162/181.4; 162/135; 162/134; 162/157.3; 162/181.6; 428/370; 428/373; 424/635; 424/649; 8/120; 8/116.1; 8/107

(58) Field of Classification Search ............. 162/181.4, 162/157.3, 181.6, 181.7, 134, 135; 428/370, 428/373, 374; 424/635, 646, 629; 8/120, 8/116.1, 107

See application file for complete search history.

(56) References Cited

U.S. PATENT DOCUMENTS

| | | | |
|---|---|---|---|
| 3,935,363 A | 1/1976 | Burkholder et al. | |
| 3,975,222 A | 8/1976 | Mesek | |
| 3,998,690 A | 12/1976 | Lyness et al. | |
| 4,259,958 A | 4/1981 | Goodbar | |
| 4,432,833 A | 2/1984 | Breese | |
| 4,469,746 A | 9/1984 | Weisman et al. | |
| 4,610,678 A | 9/1986 | Weisman et al. | |
| 4,888,238 A | 12/1989 | Katz et al. | |
| 4,952,278 A | 8/1990 | Gregory et al. | |
| 5,275,699 A | 1/1994 | Allan et al. | |
| 5,294,299 A | 3/1994 | Zeuner et al. | |
| 5,419,956 A | 5/1995 | Roe | |
| 5,427,844 A | 6/1995 | Murai et al. | |
| 5,432,000 A | 7/1995 | Young, Sr. et al. | |
| 5,492,759 A | 2/1996 | Eriksson et al. | |
| 5,547,745 A | 8/1996 | Hansen et al. | |
| 5,562,649 A | 10/1996 | Chauvette et al. | |
| 5,601,921 A | 2/1997 | Eriksson | |
| 5,611,890 A | 3/1997 | Vinson et al. | |
| 5,649,915 A | 7/1997 | Chauvette et al. | |
| 5,672,249 A | 9/1997 | Vinson et al. | |
| 5,763,333 A | 6/1998 | Suzuki et al. | |
| 5,776,308 A | 7/1998 | Sears et al. | |
| 5,833,864 A | 11/1998 | Miller et al. | |
| 5,843,061 A | 12/1998 | Chauvette et al. | |
| 5,858,172 A | 1/1999 | Sears et al. | |
| 6,074,524 A | 6/2000 | Wu et al. | |
| 6,146,494 A | 11/2000 | Seger et al. | |
| 6,159,335 A | 12/2000 | Owens et al. | |
| 6,296,737 B1 | 10/2001 | Wu et al. | |
| 6,328,850 B1 | 12/2001 | Phan et al. | |
| 6,372,333 B1 | 4/2002 | Sugiyama et al. | |
| 6,436,418 B1 | 8/2002 | Sheldon et al. | |
| 6,476,288 B1 | 11/2002 | VanRijswijck et al. | |
| 6,479,143 B1 | 11/2002 | Tamaru et al. | |
| 6,503,525 B1 | 1/2003 | Paul et al. | |
| 6,503,526 B1 | 1/2003 | Krzysik et al. | |
| 6,559,353 B1 | 5/2003 | Sheridan | |
| 6,670,035 B2 * | 12/2003 | Pittman et al. ............. 428/370 |
| 2002/0054919 A1 * | 5/2002 | Hochwalt et al. ........... 424/635 |
| 2003/0037893 A1 | 2/2003 | Simula et al. | |
| 2003/0054717 A1 | 3/2003 | Ahluwalia | |

FOREIGN PATENT DOCUMENTS

| | | |
|---|---|---|
| EP | 0 401 789 | 12/1990 |
| JP | 2000 090429 | 11/1999 |
| JP | 2001 248069 | 9/2001 |
| JP | 2004 249730 | 9/2003 |
| SE | 462918 | 7/1990 |
| WO | WO 91/05108 | 4/1991 |
| WO | WO 96/31353 | 10/1996 |
| WO | WO 02/48032 | 6/2002 |

OTHER PUBLICATIONS

Martinis, S. et al. "Absorption of liquids by dry fiber networks," *TAPPI Annual Meeting*, Chicago, 1981.

Hercules Inc. "Use of talc to make a hydrophobic low density air laid pad," *Research Disclosure*, p. 747, Nov. 1993. (Disclosure No. 35552).

NanoScale Materials Inc, Brochure: Applications of NanoActive Materials, Hydrogen Sulfide Removal, Feb. 23, 2004; URL:http://www.nanoscalematerials.com/content/nanoactive_materials/hydrogensulfideremoval.asp.

* cited by examiner

*Primary Examiner*—Mark Halpern

(57) ABSTRACT

Hydrogen sulfide is removed or reduced in absorbent products by the use of a particulate material attached to pulp fiber by a retention aid. The particulate material can remove or reduce the hydrogen sulfide in the environment surrounding the fiber. Suitable materials are zinc oxide, calcium oxide, cupric oxide, magnesium oxide, manganese dioxide, manganese oxide and aluminum oxide. Zeolites are also suitable. The particulate material may be combined with a filler prior to attachment to the fiber.

15 Claims, No Drawings

REDUCING ODOR IN ABSORBENT PRODUCTS

BACKGROUND OF THE INVENTION

Odor has always been a problem with absorbent garments such as diapers, adult incontinent products and feminine hygiene products. One of the odors generated by such products is hydrogen sulfide.

Hydrogen sulfide is usually present in very small amounts and usually not noticeable but on occasion can be detected. It is embarrassing to the parent in the case of children or to the user in the case of adults when such odors are detectable.

SUMMARY OF THE INVENTION

It is the purpose of this invention to reduce or remove hydrogen sulfide odors from the absorbent product.

It has been found that these odors may be removed by particulate materials which are certain metal oxides and certain zeolites which when present in the core of the diaper or pad appear to eliminate the odor in the liquid phase.

It is preferred that the particulate materials, the oxides and zeolites, be attached to the pulp fibers in the core of the absorbent product. They are attached by retention aids that attach the particles of material to the pulp fiber. The particulate materials considered to be effective are zinc oxide, calcium oxide, copper oxide, magnesium oxide, manganese dioxide, manganese oxide and certain zeolites.

The materials should greatly reduce and practically eliminate the hydrogen sulfide odor from absorbent products.

DETAILED DESCRIPTION

Absorbent hygienic products employing fiberized wood pulp have been available for many years. However, the tonnage used for this purpose was relatively modest until the advent of disposable diapers, first for infants and later for incontinent adults. The advent of these products and their worldwide use created an explosion in demand. The basic product leaving the papermill is most usually termed a "fluff pulp". In the United States it is most typically a fully bleached southern pine kraft process pulp produced in relatively heavy caliper, high basis weight sheets. The product is rewound into continuous rolls for shipment to the customer. Since the sheeted product is intended to be later reprocessed into individual fibers, low sheet strength is desirable and typically little or no refining is used prior to sheeting. The requirements for surface uniformity and formation are similarly moderate.

By wet forming is meant preparation of the sheet or web from a suspension in water by conventional papermaking techniques.

The pulp products of the present invention are clearly differentiated from products intended as letter, book, magazine, or similar papers. These are usually relatively highly refined to develop web strength and most have basis weights under about 100 $g/m^2$. Some specialty papers, such as cover stocks, may have basis weights that are significantly higher. Good strength is essential. Papers are normally sized to improve ink holdout and other printing properties. The products of the present invention are unsized and the strength properties such as tensile, burst, and tear strength, which are considered essential in papers, are generally much lower.

The basis weight of the products of the present invention may be as low as about 250 $g/m^2$ and are preferably at least about 550 $g/m^2$. The fiber will most usually be unrefined or only lightly refined although the invention is not so limited. Where a high surface area product is desired the fiber will normally be significantly refined. A filler is used in the present invention in an amount ranging between about 1–20% of the oven dry weight of the pulp. The higher basis weight of the products, their lower strength, and the fact that they are unsized is such as to clearly distinguish them from ordinary papers which might contain similar amounts of fillers.

The cellulose pulp of the invention may be made using conventional kraft, sulfite, chemithermomechanical or other well known processes. The furnish can be from any of various cellulose containing raw materials. Most usually these will be deciduous hardwoods; coniferous species, usually termed softwoods; or mixtures of these materials. A preferred pulp is a bleached softwood kraft pulp that would normally be intended for ultimate use as absorbent fluff. While so-called "dissolving pulps" may be used these are not preferred because of their low yield and resultant much greater cost.

Retention aids are primarily charge modifiers. They may be anionic or nonionic but are much more usually cationic materials. Depending on their manner of use, retention aids can act by making the fibers cationic or less anionic, or the filler cationic or less anionic, so there is an electrostatic attraction between filler particles and fibers. More generally the retention aids are very high molecular weight cationic water soluble polymers that act as polyelectrolytes. As such, they act as bridges linking filler particles to fibers. Typically they are polyacrylamides, polyamines, polyethyleneimines, polyamidoamines, or polyethylene oxides.

At the customer's plant, the rolls are continuously fed into a device, such as a hammermill, to be reduced as much as reasonably possible to individual fibers. The fiberized product is generally termed a cellulose "fluff". This is then continuously air laid into pads for inclusion in the intended product. U.S. Pat. No. 3,975,222 to Mesek is exemplary of such a process.

The fibers are formed into the core of a disposable diaper, disposable incontinent product or feminine hygiene product. These products will usually have a top sheet through which urine or menstrual fluid will flow, a core material, and a fluid impermeable back sheet. The core material may be of one or more layers. It can have an acquisition layer, a distribution layer and a storage layer. The layers may have different amounts and types of fibers. Each of the layers will have the individualized pulp fibers along with other material such as cross-link cellulose fibers, and superabsorbent particles. U.S. Pat. No. 6,436,418 describes a disposable diaper having certain features.

To form $H_2S$ in human urine, sulfur must be present in some form. One of several possible sulfur compounds present in human urine is L-cysteine. This molecule also occurs naturally as the dimer form cystine. According to some authorities, cystine in human urine can be found in amounts of between 0 and 130 micromoles over a 24 hour period. Since the molecular weight of cystine is 240, 130 micromoles weighs $10^{-6} \times 130 \times 240 = 0.03$ g. The average human produces about 1–1.5 liters of urine per. day so the typical maximum concentration of cystine in human urine is 0.03 g (130 micromoles) in say 1 liter or ~0.00013 molar concentration.

In order to ensure generation and detection of $H_2S$ in our laboratory tests we chose an L-cysteine concentration of either 0.05 molar (approximately 200 times (0.05/(0.00013× 2) the maximum concentration in human urine) or 0.1 molar cysteine (approximately 400 time the maximum concentration in human urine). Note that the factor of two is to account for the conversion of the dimer cystine to cysteine. These tests were not meant to represent typical conditions of urine but to insure generation and detection of $H_2S$ and to determine the effectiveness of the materials used to reduce or remove the odor. If the materials worked under these conditions then they would work under normal conditions.

Cysteine can produce $H_2S$ under the influence of bacteria with the right enzymes. One such enzyme is cystathionine lyase, whose function is aided by the co-enzyme pyridoxal 5'-phosphate. This view of the formation of $H_2S$ was tested in two experiments. It should be noted that laboratory samples of pure cysteine exist in equilibrium with levels of $H_2S$ in the gaseous headspace of the storage vessel.

EXAMPLE 1

Two 2.5 g samples of one type diaper construction were placed in a 75 ml jar, and saturated with 40 mls of either synthetic urine containing 0.1 M cysteine or a simple 0.1 M solution of cysteine This procedure was repeated with 2.5 g samples of a second type of diaper construction. The jars were sealed (lid with rubber septum) and incubated in a dark oven for 4–6 hours. After cooling, a 0.5 ml sample of headspace gas was withdrawn from the jar using a gas tight syringe and injected into a gas chromatograph (GC) with a flame photometric detector (FPD). Hydrogen sulfide was detected quantitatively and reported in ppm. The results are reported in Table 1. These $H_2S$ levels represent background $H_2S$ generation from the cysteine itself in this test at high cysteine concentrations.

TABLE 1

| Sample | Hydrogen sulfide - PPM |
|---|---|
| Diaper 1 + cysteine solution | 2.4 |
| Diaper 1 + synthetic urine & cysteine solution | 2.5 |
| Diaper 2 + cysteine solution | 1.7 |
| Diaper 2 + synthetic urine & cysteine solution | 1.5 |

EXAMPLE 2

The procedure for example 1 was repeated, but in this case only the synthetic urine containing 0.1 M cysteine was used which had been inocculated with 1.0 ml of a bacterial slurry containing large numbers of Staphylococcus aureus, Escherichia coli and Candidia albicans. The tests were performed at various pH levels. The results are reported in Table 2.

TABLE 2

| Sample | pH | Hydrogen sulfide - PPM |
|---|---|---|
| Diaper 1 + inoculated synthetic urine | 5.06 | 7300 |
| Diaper 1 + inoculated synthetic urine | 6.73 | 5000 |
| Diaper 1 + inoculated synthetic urine | 8.09 | 4300 |
| Diaper 2 + inoculated synthetic urine | 5.06 | 5900 |
| Diaper 2 + inoculated synthetic urine | 6.73 | 6400 |
| Diaper 2 + inoculated synthetic urine | 8.09 | 2900 |

From these examples it can be seen that urine, under the influence of bacteria can generate large amounts of hydrogen sulfide. Note that after the incubation period with bacteria the $H_2S$ levels are greatly increased over the background levels seen in example 1.

EXAMPLE 3

This example describes the cysteine test solution and the test procedure used in the rest of the examples.

7.5 milliliters (ml) of L-cysteine solution (aqueous, 0.05 molar (M)) was combined with 7.5 ml of Pyridoxal 5'-phosphate ("P5P", aqueous, 0.02 millimolar (mM)) and 5 ml of 2-amino-2-(hydroxymethyl)-1,3-propanediol-ethylenediaminetetraacetic acid (TRIS-EDTA) buffer solution (aqueous, 0.1M in TRIS and 0.01M in EDTA) in a 125 ml jar. The jar was sealed (lid with rubber septum) and placed in a dark oven at 30° C. for 4 hours. The jar was cooled to room temperature for 10 minutes and a 0.50 ml sample of gas was withdrawn with a gas tight syringe and injected into a gas chromatograph (GC) with a flame photometric detector (FPD). $H_2S$ was detected quantitatively and reported in PPM. In many cases $H_2S$ was not detected (ND) because it was below the limits of the apparatus.

Urine which is normally sterile becomes infected with bacteria as it comes in contact with the skin during urination. These bacteria are believed to contain enzymes capable of leading to the production of $H_2S$ from cysteine.

For laboratory convenience soil was used to provide a ready source of organisms and hence enzymes and as such provide a crude facsimile of conditions found on human skin.

We chose active organic top soil (collected from just under the leaf litter layer in a lightly wooded area) as a suitable broad spectrum source of living bacteria for "inoculation" of our $H_2S$ generating test solution. After incubating a cysteine solution with soil, $H_2S$ is readily produced. Again, the amount of $H_2S$ produced in these tests is far greater than the amounts expected to be produced in an absorbent product. The amount of $H_2S$ generated in the test solution are measured in parts per. million (ppm) and the human nose is able to detect $H_2S$ at the parts per. billion (ppb) level. Assuming that in a typical odorous diaper $H_2S$ levels are in the ppb range then if the technology described here can control these ppm levels of $H_2S$ then the amounts in an absorbent product under normal conditions can be controlled.

In each of examples 4–6 the amount of cysteine solution is the same amount as was used in example 3.

EXAMPLE 4

This describes the cysteine test.

0.125 g of the organic soil was placed in a 125 ml glass jar. The cysteine/P5P/Tris-EDTA solution of example 3 was added. After the septum sealed lid was applied the jars were swirled gently to ensure that the soil was fully wetted by the test solution. The mixture was treated under the conditions of Example 3. $H_2S$ levels in parts per million (PPM) were determined by the procedure of Example 3. There were 3 replications.

EXAMPLE 5

Example 4 was repeated except that 0.125 g zinc oxide (ZnO, Baker Analyzed® A.C.S. reagent, Product #4358-01 from J. T. Baker, Inc.) was added to the organic soil prior to adding the cysteine/P5P/Tris-EDTA solution of example 3. Again the mixture was treated under the conditions of example 3 and $H_2S$ levels in parts per million (PPM) were determined by the procedure of Example 3.

EXAMPLE 6

0.139 g of as-received retention aid Nalco 7194+ was placed in a 500 ml plastic screw top container. 13.8 g of water was added and the mixture shaken for 15 minutes. Another 125.1 g of water was added to the retention aid solution and the mixture shaken for another 15 minutes. It then stood for 5 minutes before use.

Clay slurry (Hydrafine-90 from J. M Huber Corporation) at 70% by weight solids was shaken for 15 minutes. 11.4 g of the clay slurry was then placed in a 100 ml beaker. 23.5 ml of water was added and the mixture stirred for 1 minute.

253.5 g of wet (never dried) pulp (bleached southern pine kraft pulp, grade CF 416 from Weyerhaeuser Company) at a solids content of 27.5% by weight was weighed out in a plastic beaker. The pulp was divided into halves and each half was placed in a British disintegrator. Water was added until the volume in each disintegrator was 2 liters. The disintegrators were run for about 5 minutes.

The pulp slurries were recombined in a 5 gallon bucket. Water was added until the volume in the bucket was 7 liters. A high speed Lightning brand air powered mixer was placed in the pulp slurry and run at 900 rpm to thoroughly mix the pulp.

All of the retention aid mixture was added to the pulp slurry and the mixture was stirred for 30 seconds to allow the retention aid to coat the fiber.

The clay slurry was again stirred and poured into a 1 liter beaker. 500 ml of water was added. 0.45 g zinc oxide (ZnO, Baker Analyzed® A.C.S. reagent, Product #4358-01 from J. T. Baker, Inc.) was also added. The mixture was stirred for 30 seconds.

The clay/ZnO mixture slurry was added to the pulp/retention aid suspension and stirred for 30 seconds.

The resulting mixture was poured into a square (12"×12") handsheet mold with water for a total volume of 30 liters and a handsheet was formed on a wire mesh screen. The formed sheet was couched with paper blotters, run through a laboratory felted dewatering press to a thickness of 1.3 mm and dried on an electrically heated flat handsheet drier for 15 minutes on each side to constant weight.

The pulp sheet was converted to fluff pulp by fiberizing the sheets (in portions of about 1.5g at a time) for about 30 seconds in a Waring blender on high speed to produce individualized pulp fibers. 2.5 g of the fibers was placed in a 125 ml glass jar. 0.125 grams of organic soil was added. The cysteine/P5P/Tris-EDTA solution of example 3 was added. After the septum sealed lid was applied the jar was swirled gently to ensure that the pulp and soil was fully wetted by the test solution. The mixture was treated under the conditions of Example 3. $H_2S$ levels in parts per million (PPM) were determined by the procedure of Example 3. There were 3 replications.

The results from examples 3–6 are shown in Table 3.

TABLE 3

| Sample | Hydrogen sulfide - PPM | | |
| --- | --- | --- | --- |
| Cysteine test solution only (ex. 3) | <0.31 | <0.31 | <0.31 |
| Cysteine test solution + soil (ex. 4) | 28 | 32 | 34 |
| Cysteine test solution + soil & ZnO (ex. 5) | <0.31 | <0.31 | <0.31 |
| Cysteine test solution + soil & treated pulp fibers (ex. 6) | 0.47 | 0.31 | 0.37 |

It can be seen that zinc oxide either alone or in combination with clay reduces the amount of hydrogen sulfide.

In another test a clay-zinc oxide mixture adhered to pulp fibers with retention aid reduced hydrogen sulfide from an average of 6.1 PPM to an average of 0.38 PPM. There was 6.6 g of clay and 0.66 g of ZnO to 107.25 g dry pulp. The clay was Hydrafine-90 from J. M Huber Corporation and the zinc oxide was ZnO, Baker Analyzed® A.C.S. reagent, Product #4358-01 from J. T. Baker, Inc..

Nano sized oxides were also tried. NanoActive™CaO, CaO plus, ZnO and CuO were each mixed with clay. In each case there was 0.125 g of Hydrafine-90 from J. M Huber Corporation and 0.0125 g of the NanoActive™ chemical. The CaO reduced hydrogen sulfide from an average of 2.0 PPM to an average of 0.91 PPM. The CaO plus reduced hydrogen sulfide from an average of 2.0 PPM to an average of 0.55 PPM. The ZnO and the CuO reduced hydrogen sulfide from an average of 2.0 PPM to an average of less than 0.31 PPM.

Other metallic oxides believed to reduce hydrogen sulfide are magnesium oxide, manganese dioxide, manganese oxide and aluminum oxide (aluminum trihydrate). It is thought that zeolites may also reduce the amount of hydrogen sulfide.

All of these materials may be of normal size or nano sized.

These materials are attached to the pulp fibers prior to the formation of the pulp sheet using retention aids as described above. These metal oxides and zeolites can be combined with the mineral fillers and the mixture attached to the pulp fibers with the retention aid.

Among the mineral fillers that are suitable are clays, both kaolin and bentonite; calcium carbonate such as ground chalk, limestone, or marble or precipitated calcium carbonate; and synthetic mineral fillers such as alumino-silicates or precipitated silica. It is also believed that the use of clay might act as a so-called "micro-particle retention aid" for the ZnO when used in combination. While titanium dioxide is normally used as a pigment for improving brightness it can also serve as a mineral filler. Talc (magnesium silicate) may be useful for some purposes. This is normally not preferred in the liquid storage portion of absorbent products such as diapers since it tends to decrease wicking rates and hydrophilicity. However, for some products such as oil absorbents, or where control of hydrophilicity is desired, this property can be advantageous. Certain organic fillers such as urea-formaldehyde or polystyrene microsphere types are also believed to be suitable. The term "fillers" should be construed sufficiently broadly to include those named above as well as other inorganic, organic, and synthetic inorganic filler materials in common papermaking use. Kaolin clays are the preferred fillers.

When used alone with the pulp, the amount of metal oxides or zeolites would range from 0.005 weight % to 1 weight % of the oven dry weight of the pulp. When used in conjunction with a filler, the amount of metal oxides or zeolites would range from 0.5% weight % to 50% weight % of the weight of the filler. In both cases a retention aid would be used to attach the material to the pulp fiber.

It will be understood by those skilled in the art that many variations will be possible in the products and method of their production that have not been suggested in the examples. Thus, it is the intention of the inventors that these variations should be included within the scope and spirit of the invention if they are encompassed within the following claims:

We claim:

1. A pulp fiber having a particulate material attached thereto by a retention aid, said particulate material being capable of reducing the amount of hydrogen sulfide present in the environment surrounding said pulp fiber, said particulate material being present in an amount ranging from 0.005 weight % to 1 weight % of the oven dry weight of the pulp fiber, wherein said retention aid is a water soluble polymer.

2. The pulp fiber of claim 1 in which said particulate material is selected from the group consisting of zinc oxide, calcium oxide, cupric oxide, magnesium oxide, manganese dioxide, manganese oxide and aluminum oxide.

3. The pulp fiber of claim 1 in which said particulate material is a zeolite.

4. The pulp fiber of claim 1 in which said fiber is present in the form of a pulp sheet.

5. The pulp fiber of claim 4 in which said pulp sheet is wet laid.

6. The pulp fiber of claim 5 in which said pulp sheet has a basis weight of at least 250 g/m2.

7. The pulp fiber of claim 1 in which said fiber is in an absorbent product.

8. A pulp fiber having a particulate material and a filler material attached to said fiber by a retention aid, said particulate material being capable of reducing the amount of hydrogen sulfide present in the environment surrounding said pulp fiber, said particulate material and said filler being different, wherein said retention aid is a water soluble polymer.

9. The pulp fiber of claim 8 in which said filler material is present in an amount of 1 to 20 weight percent of the oven dry weight of the fiber.

10. The pulp fiber of claim 9 in which said particulate material is present in an amount of 0.5 to 50 weight percent of the weight of said filler material.

11. The pulp fiber of claim 8 in which said fiber is present in the form of a pulp sheet.

12. The pulp fiber of claim 11 in which said pulp sheet is wet laid.

13. The pulp fiber of claim 12 in which said pulp sheet has a basis weight of at least 250 g/m2.

14. The pulp fiber of claim 8 in which said fiber is present in an absorbent product.

15. A method of making a wet laid cellulose pulp product comprising slurrying cellulose fibers in a dilute aqueous suspension, said cellulosic fibers having surfaces, using a retention aid to coat the surfaces of said fibers with at least 1%, based on the combined weight of filler material, particulate material and cellulose, of a finely divided noncellulosic filler material and a particulate material being capable of reducing the amount of hydrogen sulfide present in material surrounding said pulp fiber, wherein said retention aid is a water soluble polymer, forming the fibers into a sheet and drying the sheet.

* * * * *